(12) United States Patent
Goossen et al.

(10) Patent No.: US 6,864,394 B2
(45) Date of Patent: Mar. 8, 2005

(54) METHOD FOR PRODUCING KETONES FROM CARBOXYLIC ACID ANHYDRIDES

(75) Inventors: Lukas Goossen, Mülheim/Ruhr (DE); Keya Ghosh, Kolkata (IN)

(73) Assignee: Studiengesellschaft Kohle mbH, Mulheim/Ruhr (DE)

(*) Notice: Subject to any disclaimer, the term of this patent is extended or adjusted under 35 U.S.C. 154(b) by 0 days.

(21) Appl. No.: 10/477,653

(22) PCT Filed: May 8, 2002

(86) PCT No.: PCT/EP02/05067

§ 371 (c)(1),
(2), (4) Date: May 25, 2004

(87) PCT Pub. No.: WO02/092547

PCT Pub. Date: Nov. 21, 2002

(65) Prior Publication Data

US 2004/0186321 A1 Sep. 23, 2004

(30) Foreign Application Priority Data

May 17, 2001 (DE) ......................... 101 23 909

(51) Int. Cl.[7] .............................................. C07C 45/41
(52) U.S. Cl. ........................ 568/311; 568/314; 568/315
(58) Field of Search ................................ 568/311, 314, 568/315

(56) References Cited

U.S. PATENT DOCUMENTS 6,124,476 A    9/2000   Guram et al. ............... 549/200

OTHER PUBLICATIONS

Frost et al. Rhodium catalysed addition of boronic acids to anhydrides: a new method for the synthesis of ketones. Chemical Communications., 2001, p 2316–2317.*

Ishiyama et al. Palladium–Catalyzed Carbonylative Cross–Coupling Reaction of Arylboronic Acids with Aryl Electrophiles: Synthesis of Biaryl Ketones. Journal of Organic Chemistry., 1998, vol. 63, p 4726–4731.*

Liebeskind L.S. et al: "Thiol Ester–Boronic Acid Coupling a Mechanistically Unprecedented and General Ketone Synthesis"; Journal of the American Chemical Society; Washington, DC; Nov. 15, 2000 (pp. 11260–11261 XP000967753.

Dieter R. K.: "Reaction of Acyl Chlorides with Organometallic Reagents: A Banquet Table of Metals for Ketone Synthesis" Tetrahedron 55 (1999), Elsevier Science Publishers, Amsterdam, NL; pp. 4177–4236.

* cited by examiner

*Primary Examiner*—Johann Richter
*Assistant Examiner*—Sikarl A. Witherspoon
(74) *Attorney, Agent, or Firm*—Norris McLaughlin & Marcus PA

(57) ABSTRACT

The invention relates to a method for producing ketones by reacting boric acid derivates with carbocylic acid anhydrides in the presence of a transition metal catalyst. The carboxylic acid anhydrides can either be used in isolated form or produced from carboxylic acids in a reaction mixture. This method enables the simple embodiment of a multitude of functionalized ketones in a single reaction step.

16 Claims, No Drawings

METHOD FOR PRODUCING KETONES FROM CARBOXYLIC ACID ANHYDRIDES

This application is a 371 of PCT/EP02/05067 filed on May 8, 2002, which claims priority of German Application No. 101 23 909.2 filed on May 17, 2001.

The invention relates to a process for preparing ketones by reacting carboxylic anhydrides with boronic acid derivatives in the presence of a transition metal catalyst. The carboxylic anhydrides may either be used in isolated form or generated in a reaction mixture of carboxylic acids. This process enables the simple preparation of a multitude of functionalized ketones in a single reaction step.

Keto groups are important functional groups in a series of pharmacologically important compounds such as ethacrynic acid, celioprolol, tolperisone, aceperone, and many others. A mild and efficient process for introducing keto groups into sensitive functionalized molecules is therefore of high interest.

Aryl alkyl ketones are generally obtained by Friedel-Crafts acylation, but only certain substitution patterns on the aromatic ring are obtainable by this method and isomer mixtures which are difficult to separate are often obtained (see, for example, J. March, Advanced Organic Chemistry, Wiley, N.Y., 3rd Edition, 1985, 484–487, 496–497).

Aside from this, the addition of carbon nucleophiles to carboxylic acid derivatives has been found to be useful for synthesizing ketones. However, the direct conversion of carboxylic acids to ketones is only known with a few highly reactive carbon nucleophiles, for example alkyllithium compounds. When suitable reaction conditions are selected, the reaction remains at the stage of the ketones without forming the tertiary alcohols. Common methods are described, for example, in M. J. Jorgenson, Org. React. 1970, 18, 1–97; G. M. Rubottom, C. Kim, J. Org. Chem. 1983, 48, 1550; or Y. Ahn, T. Cohen, Tetrahedron Lett. 1994, 35, 203–206.

A disadvantage is that only a few functional groups are tolerated under these conditions.

A more common variant is the reaction of carbon nucleophiles with reactive carboxylic acid derivatives, for example nitriles, acid chlorides or Weinreb amides. In some cases these have to be prepared first from the carboxylic acids in an additional reaction step. Many carbon nucleophiles can be utilized for this reaction, for example Grignard reagents, organolithium compounds, cuprates or organozinc compounds. There is a review in F. A. Carey, R. J. Sundberg, *Organische Chemie*, VCH, Weinheim, 1995, 1105–1248. Some examples of such reactions are shown in Scheme 1.

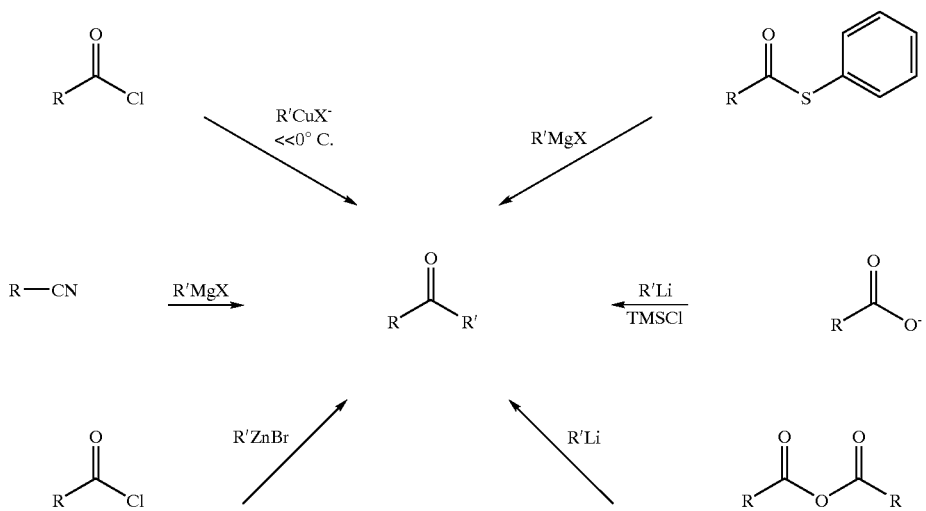

Scheme 1. Traditional syntheses of ketones from carboxylic acid derivatives.

A disadvantage of the use of Grignard reagents and organolithium compounds is that there must be no sensitive functional groups in the organometallic or the carbonyl components. Only C=C double bonds, alkoxy or acetal groups are tolerated, whereas, for example, OH, NH, C=O, $NO_2$ and CN groups, and also acidic C—H groups, lead to side reactions.

Substantially more tolerant toward functional groups are organozinc compounds, as described, for example, in P. Knochel, R. D. Singer, *Chem. Rev.* 1993, 93, 2117 or F. A. Carey, R. J. Sundberg, *Organische Chemie*, VCH, Weinheim, 1995, 1128–1132. However, a disadvantage is that they can often be obtained only indirectly, for example from the Grignard compounds, and, as a consequence of their oxygen and moisture sensitivity, they are not easy to handle. On this subject, see J. Boersma, *Comprehensive Organic Chemistry*, G. Wilkinson (Ed.), Pergamon Press, Oxford, 1982, 1974 or P. T. Li, T. P. Burns, S. T. Uhm, *J. Org. Chem.* 1981, 46, 4323.

Cuprates, which are described, for example, in J. F. Normant, *Synthesis*, 1972, 63–80: G. H. Posner, *An Introduction to Synthesis using Organocopper Reagents*, Wiley, N.Y., 1980, 68–81; O. P. Vig, S. D. Sharma, J. C. Kapur, *J. Ind. Chem. Soc.* 1969, 46, 167; A. E. Jukes, S. S. Dua, H. Gilman, *J. Organomet. Chem.* 1970, 21, 241, are likewise compatible with many functional groups, but generally first have to be prepared from more reactive compounds.

Tin and cadmium compounds too can be selectively reacted with carboxylic acid derivatives, see, for example: P. R. Jones, P. J. Desio, *Chem. Rev.* 1978, 78, 491; E. R. Burkhardt, R. D. Rieke, *J. Org. Chem.* 1985, 50, 416; J. Cason, F. S. Prout, *Org. Synth. III* 1955, 601, but their use is strictly limited by their toxicity.

Aside from uncatalyzed coupling reactions, transition metal-catalyzed cross-coupling reactions, for example with the metals Cu, Ni, Pd, Pt, are also important.

It is known that boronic acid derivatives are advantageous starting materials for cross-couplings, since, as a consequence of their low toxicity and their insensitivity toward air and moisture, unlike, for example, the aforementioned Grignard compounds or zinc compounds, they can also be stored in pure form and are easy to handle. Boronic acid pinacol esters can even be distilled and chromatographed.

Numerous alkyl-, vinyl-, aryl- or heteroarylboronic acid derivatives are obtainable in a simple manner, for example, by substituting aromatics with boric esters in the presence of Lewis acids, by reacting other organometallic compounds with boric esters or by palladium-catalyzed coupling reactions, for example of bispinacoldiboron or pinacolborane with vinyl, aryl or heteroaryl halides or triflates. In the latter reactions, a wide variety of functional groups is tolerated.

Various palladium-catalyzed ketone syntheses from boronic acids are described in the literature. In these syntheses, reactive carboxylic acid derivatives are reacted with boronic acids in the presence of palladium complexes to give ketones. Specifically, the cross-coupling of carbonyl chlorides, carboxylic thioesters and perfluorinated phenol carboxylates is known.

A disadvantage of the use of carbonyl chlorides is that they first have to be prepared from the carboxylic acids and an aggressive chlorinating agent, generally thionyl chloride, in a separate reaction step (R. K. Dieter, *Tetrahedron* 1999, 55, 4177–4236; M. P. Sibi, *Org. Prep. Proced. Int.* 1993, 25, 15–40; V. Farina, V. Krishnamurthy, W. Scott in *Organic Reactions*, Wiley, N.Y., 1997, Vol. 50, 1–652). Accordingly, it is also only possible to prepare derivatives which are stable under the reaction conditions mentioned. The cross-couplings of carbonyl chlorides require the addition of stoichiometric amounts of base, and large amounts of inorganic salts are inevitably by-produced, whose removal and disposal causes high costs. A further disadvantage is that the hydrolysis sensitivity of the carbonyl chlorides entails strict exclusion of water in the reaction.

L. Liebeskind et al. report a process by which thio esters can be reacted under palladium catalysis with boronic acids to give ketones (L. Liebeskind, J. Srogl, *J. Am. Chem. Soc.* 2000, 122, 11260–11261). Even sensitive ketones can be prepared in good yields by this method. A disadvantage is that stoichiometric amounts of copper in the form of an expensive thiophenecarboxylate have to be used. During the process, large amounts of copper wastes are formed which cause high costs in their disposal. A further disadvantage is that the preformation of the thioesters from odor-intensive and toxic thiols in an additional reaction step is necessary for this process.

Yamamoto et al. have reported that phenol perfluoroalkylcarboxylates can be reacted under palladium catalysis with boronic acids to give perfluoroalkyl ketones (R. Kakino, I. Shimizu, A. Yamamoto, *Bull. Chem. Soc. Jp.* 2001, 74, 371–376). However, the reaction is limited to highly reactive perfluorocarboxylic esters and cannot be applied to other carboxylic acid derivatives. A further disadvantage is that the phenol esters cannot be generated in situ.

There is therefore a need for a general process in which comparatively unreactive carboxylic acid derivatives which are comparatively simple to prepare from the carboxylic acids can be reacted with boronic acid derivatives to give ketones, said process featuring ease of performability, mild reaction conditions, low waste production and the use of inexpensive reagents which pose no health risk.

Surprisingly, a process has now been found for preparing ketones 3 from carboxylic anhydrides 1 and boronic acid derivatives 2, which is characterized in that the reaction is carried out in the presence of a palladium catalyst (Scheme 2). Aside from Pd, useful metals are also those which are known to be suitable for the other cross-coupling reactions, for example Ni, Pt, Cu.

Scheme 2.
Conversion of carboxylic anhydrides to ketones

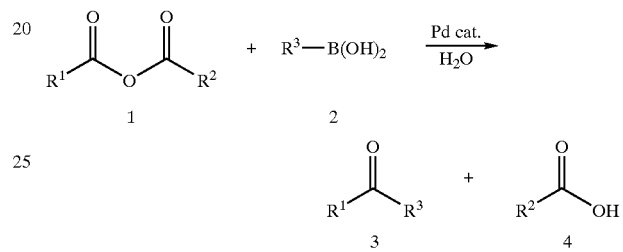

In contrast to the abovementioned processes in which carbonyl chlorides or carboxylic thioesters are used, the process according to the invention surprisingly requires no base. This is advantageous since the material costs are reduced and the isolation of the products is simplified.

In comparison to carbonyl chlorides, carboxylic anhydrides are distinctly less reactive and, unlike carbonyl chlorides, in the absence of a base, they react only very slowly, if at all, with functional groups, for example OH groups. The discovery of a cross-coupling of carboxylic anhydrides in the absence of a base is particularly surprising, since similar reaction behavior might also be expected for the addition over a palladium catalyst.

The only by-products formed in the process according to the invention are carboxylic acids and boric acid or their derivatives. The carboxylic acids can be removed by distillation or extraction and can be converted back to the corresponding anhydrides by a multitude of known processes and thus recycled. This distinctly reduces the amount of waste in the process according to the invention compared to the abovementioned standard processes. This constitutes a further advantage compared to the traditional process.

If desired, the anhydrides can also be generated in situ in the process according to the invention from the carboxylic acids 4, which are readily available in a large number, and a carboxylic anhydride 5 (Scheme 3). Which of the two possible ketones 3 and 7 is formed is determined by the size of the $R^i$ radicals: when $R^2$ is more sterically demanding than $R^1$, the ketone 3 is formed in very high selectivity. The by-product in this process variant according to the invention is a carboxylic acid, which can be recycled back to the corresponding anhydride by known processes. This variant is advantageous especially when the carboxylic acid 4 to be converted is expensive.

Scheme 3.
Conversion of carboxylic acids to ketones

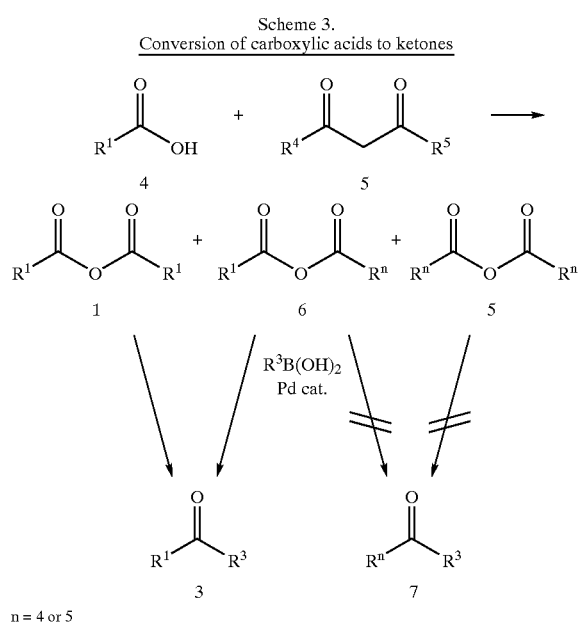

n = 4 or 5

This last-mentioned process variant, in comparison to other direct conversions of carboxylic acids to ketones, features in particular substantially simplified reaction conditions and a distinctly wider substrate spectrum. For the first time, this process allows carboxylic acids having base-sensitive groups, for example phenol esters, to be converted to ketones in a single process step. Compared to the existing palladium-catalyzed conversions of boronic acid derivatives to ketones, it is advantageous that a process step is saved.

It has also been observed that, surprisingly, a low water content in the reaction mixture is not disadvantageous as in the analogous conversion of carbonyl chlorides, but rather actually supports the conversions and selectivities of the reaction. This is particularly surprising in that anhydrides are also hydrolyzed slowly by water, and yield losses would thus actually have to be expected in the event of water addition. This fact also results in a further advantage of the process according to the invention compared to the carbonyl chloride processes, since hydrous solvents are substantially less expensive than anhydrous solvents.

In the process according to the invention, carboxylic anhydrides of the general formula 1 are used, or are generated in situ from carboxylic acids of the general formula 2 and carboxylic anhydrides of the general formula 3.

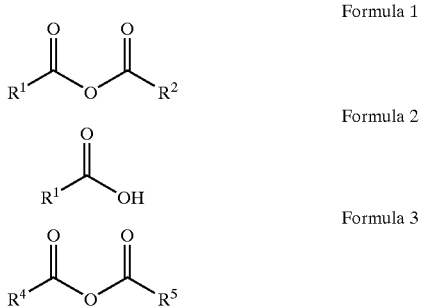

Formula 1

Formula 2

Formula 3

The substituents $R^1$ and $R^2$ can each independently be selected from the group of hydrogen, linear and branched $C_1$–$C_{14}$-alkyl, aryl, vinyl or heteroaryl from the group of pyridine, pyrimidine, pyrrole, thiophene, furan, and may themselves bear further substituents from the group of linear and branched $C_1$–$C_8$-alkyl or $C_1$–$C_{10}$-aryl or heteroaryl, linear and branched $C_1$–$C_8$-alkyloxy or $C_1$–$C_8$-aryloxy, halogenated linear and branched $C_1$–$C_8$-alkyl or halogenated $C_1$–$C_{10}$-aryl or heteroaryl, linear and branched $C_1$–$C_8$-alkyl- or $C_1$–$C_8$-arylaminocarbonyl, linear and branched $C_1$–$C_8$-alkylaminocarbonyl, linear and branched $C_1$–$C_8$-dialkylamino, $C_1$–$C_8$-arylamino, $C_1$–$C_8$-diarylamino, formyl, hydroxyl, carboxyl, cyano and halogens such as F, Cl, Br and I.

In the process variant according to the invention of Scheme 2, in which isolated anhydrides are used, preference is given to using carboxylic anhydrides of the general formula 1 in which both substituents $R^1$ and $R^2$ are the same.

In the process variant according to the invention of Scheme 3, carboxylic acids of the general formula 2 in which $R^1$ can be selected from the group of hydrogen, linear and branched $C_1$–$C_{14}$-alkyl, aryl, vinyl or heteroaryl from the group of pyridine, pyrimidine, pyrrole, imidazole, oxazole, thiophene, furan, and may itself bear further substituents from the group of linear and branched $C_1$–$C_8$-alkyl or $C_1$–$C_8$-aryl, linear and branched $C_1$–$C_8$-alkyloxy or $C_1$–$C_8$-aryloxy, halogenated linear and branched $C_1$–$C_8$-alkyl or halogenated $C_1$–$C_{10}$-aryl or heteroaryl, linear and branched $C_1$–$C_8$-alkyl- or $C_1$–$C_8$-arylaminocarbonyl, linear and branched $C_1$–$C_8$-alkylaminocarbonyl, linear and branched $C_1$–$C_8$-dialkylamino, $C_1$–$C_8$-arylamino, $C_1$–$C_8$-diarylamino, formyl, hydroxyl, carboxyl, cyano and halogens such as F, Cl, Br and I, are activated with anhydrides of the general formula 3 in which the substituents $R^4$ and $R^5$ can each independently be selected from the group of hydrogen, linear and branched $C_1$–$C_{14}$-alkyl, aryl, vinyl or heteroaryl from the group of pyridine, pyrimidine, pyrrole, imidazole, oxazole, thiophene, furan, and may themselves bear further substituents from the group of linear and branched $C_1$–$C_8$-alkyl or $C_1$–$C_{10}$-aryl or heteroaryl, linear and branched $C_1$–$C_8$-alkyloxy or $C_1$–$C_8$-aryloxy, halogenated linear and branched $C_1$–$C_8$-alkyl or halogenated $C_1$–$C_8$-aryl, linear and branched $C_1$–$C_8$-alkyl- or $C_1$–$C_8$-arylaminocarbonyl, linear and branched $C_1$–$C_8$-alkylaminocarbonyl, linear and branched $C_1$–$C_8$-dialkylamino, $C_1$–$C_8$-arylamino, $C_1$–$C_8$-diarylamino, formyl, hydroxyl, carboxyl, cyano and halogens such as F, Cl, Br and I.

In the process variant of Scheme 3, the carboxylic acids are preferably activated using anhydrides of the general formula 3 which themselves, compared to the transition metal catalyst, only exhibit a low reactivity for the reaction of Scheme 1. Particular preference is given to using carboxylic anhydrides of the general formula 3 in which both substituents $R^4$ and $R^5$ are branched in the α-position to the carboxyl group. Very particular preference is given to using pivalic anhydride.

The reaction partners used are boronic acids and their derivatives of the general formula 4 where $Z^1$ and $Z^2$ are substituents from the group of hydroxyl, dialkylamino, $C_1$–$C_8$-alkyloxy, aryloxy, fluorine, bromine, chlorine, iodine. The $Z^1$ and $Z^2$ radicals may also be joined together by a C—C bond or via a linear or branched alkyl or aryl bridge. The $R^3$ substituent is an alkyl, aryl, vinyl or heteroaryl radical from the group of pyridine, pyrimidine, pyrrole, pyrazole, imidazole, oxazole, thiophene, furan, which may itself bear further substituents from the group of linear and branched $C_1$–$C_8$-alkyl or $C_1$–$C_8$-aryl, vinyl or heteroaryl from the group of pyridine, pyrimidine, pyrrole, pyrazole, imidazole, oxazole, thiophene, furan, linear and branched $C_1$–$C_8$-alkyloxy or $C_1$–$C_8$-aryloxy, halogenated linear and branched $C_1$–$C_8$-alkyl or halogenated $C_1$–$C_8$-aryl, linear and branched $C_1$–$C_8$-alkyl- or $C_1$–$C_8$-aryloxycarbonyl, linear and branched $C_1$–$C_8$-alkyl- or $C_1$–$C_8$-arylcarbonyl, linear and branched $C_1$–$C_8$-alkylamino, linear and branched $C_1$–$C_8$-dialkylamino, $C_1$–$C_8$-arylamino, $C_1$–$C_8$-diarylamino, formyl, hydroxyl, carboxyl, cyano, amino and halogens such as F, Cl, Br and I.

Formula 4

If desired, the boronic acids can be generated in situ by reacting appropriate vinyl halides, aryl halides or heteroaryl halides, or vinyl, aryl or heteroaryl pseudohalides, either with a diboron compound or a borane in the presence of a palladium catalyst according to the prior art.

The catalysts used in the process according to the invention are preferably common palladium(II) salts such as palladium chloride, bromide, iodide, acetate, acetylacetonate, which may optionally be stabilized by further ligands, for example phosphines, alkylnitriles, ketones, or Pd(0) species, for example palladium on activated carbon or tris(dibenzylideneacetone)dipalladium.

Particular preference is given to generating the palladium catalysts in situ from common palladium(II) salts such as palladium chloride, bromide, iodide, acetate, acetylacetonate, or from Pd(0) species such as palladium on activated carbon or tris(dibenzylideneacetone)dipalladium, by adding phosphine ligands $PR^1R^2R^3$ where $R^i$ are substituents from the group of hydrogen, linear and branched $C_1$–$C_8$-alkyl, aryl, vinyl or heteroaryl from the group of pyridine, pyrimidine, pyrrole, thiophene, furan, which may themselves be substituted by further substituents from the group of linear and branched $C_1$–$C_8$-alkyl or $C_1$–$C_8$-aryl, linear and branched $C_1$–$C_8$-alkyloxy or $C_1$–$C_8$-aryloxy, halogenated linear and branched $C_1$–$C_8$-alkyl or halogenated $C_1$–$C_8$-aryl, linear and branched $C_1$–$C_8$-alkyl- or $C_1$–$C_8$-aryloxycarbonyl, linear and branched $C_1$–$C_8$-alkylamino, linear and branched $C_1$–$C_8$-dialkylamino, $C_1$–$C_8$-arylamino, $C_1$–$C_8$-diarylamino, formyl, hydroxyl, carboxyl, cyano and halogens such as F, Cl, Br and I. Alternatively, defined palladium complexes which have been generated beforehand from the abovementioned ligands in one or more process steps can also be used.

In the process according to the invention, from 1 to 20 equivalents of phosphine are used based on the amount of transition metal used, preferably from 1 to 4 equivalents.

In the process according to the invention, an amount of catalyst of from 0.001 mol % to 20 mol % is used, based on the acetic acid derivative. Preference is given to using an amount of catalyst of from 0.01 mol % to 3 mol %.

The process according to the invention is carried out at temperatures of from −20° C. to 150° C., preferably from 20° C. to 100° C. and more preferably from 40° C. to 70° C.

The process according to the invention can be carried out in the presence of a solvent or without solvent. Preference is given to working in the presence of a solvent. Preferred solvents are water, saturated aliphatic hydrocarbons, alicyclic hydrocarbons, aromatic hydrocarbons, alcohols, amides, sulfoxides, sulfonates, nitriles, esters or ethers.

For example, the solvents used may be pentane, hexane, heptane, octane, cyclohexane, benzene, toluene, xylenes, ethylbenzene, mesitylene, dioxane, tetrahydrofuran, diethyl ether, dibutyl ether, methyl t-butyl ether, diisopropyl ether, diethylene glycol dimethyl ether, methanol, ethanol, propanol, isopropanol, methyl acetate, ethyl acetate, t-butyl acetate, dimethylformamide, diethylformamide, N-methylpyrrolidone, dimethylacetamide, dimethyl sulfoxide, sulfolane, acetonitrile, propionitrile or water.

Preference is given to using aromatic hydrocarbons, amides, esters and ethers. Particular preference is given to using ethers.

Preference is given to carrying out the process according to the invention in the presence of water. Particular preference is given to working in the presence of from 0.1 to 100 equivalents of water based on the boronic acid derivative. The water present in the solvent and in the reagents has to be taken into account. Very particular preference is given to adding from 2 to 20 equivalents of water.

Preference is given to carrying out the process according to the invention in such a way that the solids and a portion of the solvent are initially charged and the liquid starting materials are metered in with a further portion of the solvent.

To isolate the ketones prepared in accordance with the invention, the reaction mixture is worked up on completion of the reaction preferably by distillation and/or by extraction or crystallization.

EXAMPLES

Example 1

Preparation of 3-phenylpropyl phenyl ketone: A 100 ml flask having a septum cap and magnetic stirrer was initially charged with palladium acetate (67.3 mg, 0.30 mmol), diphenylferrocenylphosphine (194 mg, 0.35 mmol), 3-phenylpropionic acid (1.50 g, 10 mmol) and benzeneboronic acid (1.46 g, 12 mmol). THF (40 ml), water (45 mg, 2.5 mmol) and pivalic anhydride (2.79 g, 15 mmol) were added in succession with the aid of syringes. The reaction vessel was then purged with inert gas and the reaction mixture was heated to 60° C. for a few hours. The progress of the reaction was followed with the aid of gas chromatography. As soon as complete conversion had been attained, the catalyst was removed by filtration through silica gel, the solvent was distilled off and the residue was recrystallized from hexane. The pivalic acid remained in the mother liquor and could be recovered. In this way, 1.73 g (83%) of 3-phenylpropyl phenyl ketone were obtained as colorless crystals. $^1$H NMR (200 MHz, CDCl$_3$, 25° C., TMS): δ=7.95 (m, 2H), 7.61–7.19 (m, 8H), 3.32 (t, $^3$J(H,H)=6 Hz, 2H), 3.13 (t, $^3$J (H,H)=6 Hz, 2H) ppm; $^{13}$C NMR (50 MHz, CDCl$_3$, 25° C., TMS): δ=198.8, 141.0, 136.5, 132.7, 128.3, 128.2, 128.1, 127.7, 125.8, 40.1, 29.8 ppm; MS (70 eV): m/z (%): 210(53) [M$^+$], 105(100), 77(46), 51(17), HRMS: calc. for $C_{15}H_{14}O$ [M$^+$]: 210.104465; found: 210.10447; anal. calc. for $C_{15}H_{14}O$ (210.3): C 85.68%; H 6.71%; N 0.00%; found: C 85.37; H 6.67; N 0.00%.

Comparative Examples 2–10

In each case 1 mmol of hexanoic anhydride was heated to to 60° C. for 16 h with 1.2 mmol of benzeneboronic acid, 0.03 mmol of Pd(OAc)$_2$, 0.07 mmol of ligand (0.035 mmol in the case of chelate ligands) and the appropriate amount of water. The yields were determined by gas chromatography.

The results are compiled in Table 1.

TABLE 1

Reaction of hexanoic anhydride with benzeneboronic acid.

| Ex. | Ligand | Solvent | Water (mmol) | Yield (%) |
|---|---|---|---|---|
| 2 | PPh$_3$ | THF | 0 | 29 |
| 3 | PPh$_3$ | THF | 2.5 | 97 |
| 4 | PPh$_3$ | THF | 10 | 38 |
| 5 | PPh$_3$ | DME | 2.5 | 53 |
| 6 | PPh$_3$ | DMF | 2.5 | 92 |
| 7 | PPh$_3$ | toluene | 2.5 | 77 |
| 8 | PPh$_3$ | CH$_3$CN | 2.5 | 54 |
| 9[a] | PPh$_3$ | THF | 2.5 | 92 |
| 10 | PCy$_3$ | THF | 2.5 | 91 |
| 11 | P(o-Tol)$_3$ | THF | 2.5 | 31 |
| 12 | BINAP | THF | 2.5 | <5 |
| 13 | P(p-MeOPh)$_3$ | THF | 2.5 | 97 |
| 14 | DPPF | THF | 2.5 | <5 |
| 15 | P(Fur)$_3$ | THF | 2.5 | 46 |
| 16 | P(t-Bu)$_3$ | THF | 2.5 | 28 |

[a] at 20° C.

Examples 17 to 28

Preparation of aryl ketones R$^1$—CO—R$^3$ from carboxylic anhydrides R$^1$—COOCO—R$^1$ and boronic acids R$^3$B(OH)$_2$.

In each case 1 mmol of carboxylic anhydride was heated to to 60° C. for 16 h with 1.2 mmol of boronic acid, 0.03 mmol of Pd(OAc)$_2$, 0.07 mmol of tri(p-methoxyphenyl) phosphine and 2.5 mmol of water in 4 ml of THF. The products were worked up by column chromatography (SiO$_2$ or basic Al$_2$O$_3$, hexane/ethyl acetate) and characterized by $^1$H and $^{13}$C NMR, GC-MS and HRMS. The results are compiled in Table 2. The yields quoted relate to isolated products.

TABLE 2

Preparation of various ketones from anhydrides.

| Ex. | R$^1$ | R$^3$ | Yield (%) |
|---|---|---|---|
| 17 | n-C$_5$H$_{11}$ | o-tolyl | 98 |
| 18 | n-C$_5$H$_{11}$ | p-MeO-phenyl | 91 |
| 19[a] | n-C$_5$H$_{11}$ | p-CH$_3$CO-phenyl | 96 |
| 20 | n-C$_5$H$_{11}$ | m-Cl-phenyl | 97 |
| 21 | n-C$_5$H$_{11}$ | 2-furyl | 84 |
| 22 | n-C$_5$H$_{11}$ | 3-thienyl | 88 |
| 23 | CH$_3$ | phenyl | 98 |
| 24 | i-butyl | phenyl | 98 |
| 25 | —C(CH$_3$)=CH$_2$ | phenyl | 71 |
| 26[b] | p-MeO-Ph | phenyl | 90 |
| 27[b] | phenyl | phenyl | 96 |
| 28 | t-butyl | phenyl | <5 |

[a] 0.07 mmol of PCy$_3$ as ligand.
[b] 0.07 mmol of PPh$_3$ as ligand.

Examples 29–46

Preparation of aryl ketones R$^1$—CO—R$^3$ from carboxylic acids R$^1$—COOH and boronic acids R$^3$B(OH)$_2$ in the presence of pivalic anhydride.

In each case 1 mmol of carboxylic acid was heated to 60° C. in 4 ml of THF for 16 h with 1.5 mmol of pivalic anhydride, 1.2 mmol of boronic acid, 0.03 mmol of Pd(OAc)$_2$, 0.07 mmol of ligand (0.035 mmol for chelate phosphines) and 2.5 mmol of water. The products were worked up by column chromatography (SiO$_2$ or basic Al$_2$O$_3$, hexane/ethyl acetate) and characterized by $^1$H and $^{13}$C NMR, GC-MS and HRMS. The results are compiled in Table 3. The yields quoted relate to isolated products.

TABLE 3

Preparation of ketones from carboxylic acids.

| Ex. | Product[a] | Ligand[b] | Yield (%) |
|---|---|---|---|
| 29 | phenyl-CO-CH$_2$-CH(CH$_3$)$_2$ | A | 90 |
| 30[c] | phenyl-CO-cyclohexyl | A | 60 |
| 31 | phenyl-CO-CH$_2$-CH$_2$-CO-CH$_3$ | A | 65 |

TABLE 3-continued

Preparation of ketones from carboxylic acids.

| Ex. | Product[a] | Ligand[b] | Yield (%) |
|-----|------------|-----------|-----------|
| 32 | [steroid-derived diketone structure with phenyl ketone side chain] | A | 81 |
| 33 | benzophenone | C | 68 |
| 34 | 4-cyanobenzophenone | B | 80 |
| 35 | 4-nitrobenzophenone | C | 75 |
| 36 | 4-acetylbenzophenone | D | 54 |
| 37 | 4-acetamidobenzophenone | B | 85 |
| 38 | 3-acetoxybenzophenone | D | 48 |
| 39 | 4-methoxybenzophenone | D | 55 |

TABLE 3-continued

Preparation of ketones from carboxylic acids.

| Ex. | Product[a] | Ligand[b] | Yield (%) |
|---|---|---|---|
| 40 | *2-methyl-1-phenyl-3-phenylpropan-1-one structure* | C | 65 |
| 41 | *3-hydroxybenzophenone structure* | A | 43 |
| 42 | *4-methoxyphenyl 2-phenylethyl ketone structure* | A | 78 |
| 43 | *4-acetylphenyl 2-phenylethyl ketone structure* | D | 55 |
| 44 | *1-naphthyl 2-phenylethyl ketone structure* | C | 75 |
| 45 | *3-thienyl 2-phenylethyl ketone structure* | A | 72 |
| 46 | *2-furyl 2-phenylethyl ketone structure* | B | 47 |

[a]$R^3$ radicals from the boronic acids are placed on the left-hand side of the keto group;
[b]Ligands: A: P(p-MeOPh)$_3$; B: PPh$_3$; C: DPPF; D: PCy$_3$;
[c]DME as solvent.

Examples 47 and 48

Preparation of aryl ketones $R^1$—CO—$R^3$ from carboxylic acids $R^1$—COOH and boronic acids $R^3B(OH)_2$ in the presence of carbonic anhydrides.

1 mmol of benzoic acid was heated to 60° C. in 4 ml of THF for 16 h with 2 mmol of dimethyl dicarbonate (Example 47) or di-t-butyl dicarbonate (Example 48), 1.2 mmol of benzeneboronic acid, 0.03 mmol of Pd(OAc)$_2$, 0.07 mmol of tri(p-methoxyphenyl)phosphine and 2.5 mmol of water. The product isolated was benzophenone in a 91% yield (Example 47) or 24% (Example 48). The spectroscopic data of the products were identical to those from Example 33. The carbonic acid derivatives by-produced (monomethyl carbonate or t-butyl carbonate) decomposed under the reaction conditions to give $CO_2$ and methanol or t-butanol.

What is claimed is:

1. A process for preparing ketones comprising reacting boronic acid derivatives with carboxylic anhydrides, wherein the reaction is carried out in the presence of a transition metal catalyst and the transition metal used is one from the group consisting of Pd, Ni, Pt and Cu.

2. The process of claim 1, wherein the transition metal used is Pd.

3. The process of claim 1, wherein the reaction is carried out in the presence of water.

4. The process of claim 1, wherein the anhydrides are prepared in situ from the corresponding carboxylic acids.

5. The process of claim 4, wherein the anhydrides are generated in situ by reacting carboxylic acids with anhydrides.

6. The process of claim 1, wherein the reaction is carried out with carboxylic anhydrides of the general formula 1

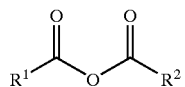

1 where the substituents $R^1$ and $R^2$ are each independently selected from the group consisting of hydrogen, linear and branched $C_1$–$C_{14}$-alkyl, aryl, vinyl or heteroaryl selected from the group consisting of pyridinyl, pyrimidinyl, pyrrolyl, thiophenyl, and furanyl, and may themselves bear further substituents selected from the group consisting of linear and branched $C_1$–$C_8$-alkyl or $C_1$–$C_{10}$-aryl or heteroaryl, linear and branched $C_1$–$C_8$-alkyloxy or $C_1$–$C_8$-aryloxy, halogenated linear and branched $C_1$–$C_8$-alkyl or halogenated $C_1$–$C_{10}$-aryl or heteroaryl, linear and branched $C_1$–$C_8$-alkyl- or $C_1$–$C_8$-arylaminocarbonyl, linear and branched $C_1$–$C_8$-alkylaminocarbonyl, linear and branched $C_1$–$C_8$-dialkylamino, $C_1$–$C_8$-arylamino, $C_1$–$C_8$-diarylamino, formyl, hydroxyl, carboxyl, cyano, nitro and halogens.

7. The process of claim 4, wherein the carboxylic acids used are those of the general formula 2

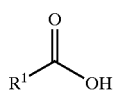

2 where the substituent $R_1$ is selected from the group consisting of hydrogen, linear and branched $C_1$–$C_{14}$-alkyl, aryl, vinyl or heteroaryl selected from the group consisting of pyridinyl, pyrimidinyl, pyrrolyl, thiophenyl, and furanyl, and may itself bear further substituents selected from the group consisting of linear and branched $C_1$–$C_8$-alkyl or $C_1$–$C_{10}$-aryl or heteroaryl, linear and branched $C_1$–$C_8$-alkyloxy or $C_1$–$C_8$-aryloxy, halogenated linear and branched $C_1$–$C_8$-alkyl or halogenated $C_1$–$C_{10}$-aryl or heteroaryl, linear and branched $C_1$–$C_8$-alkyl- or $C_1$–$C_8$-arylaminocarbonyl, linear and branched $C_1$–$C_8$-alkylaminocarbonyl, linear and branched $C_1$–$C_8$-dialkylamino, $C_1$–$C_8$-arylamino, $C_1$–$C_8$-diarylamino, formyl, hydroxyl, carboxyl, cyano, nitro and halogens.

8. The process of claim 5, wherein the carboxylic acids are reacted in situ with carboxylic anhydrides of the formula 3

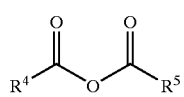

3 where the substituents $R^3$ and $R^4$ can each independently be selected from the group consisting of hydrogen, linear and branched $C_1$–$C_{14}$-alkyl, aryl, vinyl or heteroaryl selected from the group consisting of pyridinyl, pyrimidinyl, pyrrolyl, thiophenyl, and furanyl, and may themselves bear further substituents selected from the group consisting of linear and branched $C_1$–$C_8$-alkyl or $C_1$–$C_{10}$-aryl or heteroaryl, linear and branched $C_1$–$C_8$-alkyloxy or $C_1$–$C_8$-aryloxy, halogenated linear and branched $C_1$–$C_8$-alkyl or halogenated $C_1$–$C_{10}$-aryl or heteroaryl, linear and branched $C_1$–$C_8$-alkyl- or $C_1$–$C_8$-arylaminocarbonyl, linear and branched $C_1$–$C_8$-alkylaminocarbonyl, linear and branched $C_1$–$C_8$-dialkylamino, $C_1$–$C_8$-arylamino, $C_1$–$C_8$-diarylamino, formyl, hydroxyl, carboxyl, cyano, nitro and halogens.

9. The process of claim 1, in which boronic acid derivatives of the general formula 4 are used

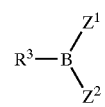

4 where $Z^1$ and $Z^2$ are substituents selected from the group consisting of hydroxyl, dialkylamino, $C_1$–$C_8$-alkyloxy, aryloxy, fluorine, bromine, chlorine, and iodine, which may be joined together via a C—C bond or via a linear or branched alkyl chain, a vinyl group or an aryl group, $R^3$ is an alkyl, aryl, vinyl or heteroaryl radical selected from the group consisting of pyridinyl, pyrimidinyl, pyrrolyl, thiophenyl, and furanyl, which may itself bear further substituents selected from the group consisting of linear and branched $C_1$–$C_8$-alkyl or $C_1$–$C_8$-aryl, linear and branched $C_1$–$C_8$-alkyloxy or $C_1$–$C_8$-aryloxy, halogenated linear and branched $C_1$–$C_8$-alkyl or halogenated $C_1$–$C_8$-aryl, linear and branched $C_1$–$C_8$-alkyl- or $C_1$–$C_8$-aryloxycarbonyl, linear and branched $C_1$–$C_8$-alkylamino, linear and branched $C_1$–$C_8$-dialkylamino, $C_1$–$C_8$-arylamino, $C_1C_8$-diarylamino, formyl, hydroxyl, carboxyl, cyano, F, Cl, Br and I.

10. The process of claim 2, wherein the palladium catalyst is generated from a palladium (II) salt and a phosphine ligand $PR^1R^2R^3$ where $R^1$, $R^2$ and $R^3$ are substituents selected from the group consisting of hydrogen, linear and branched $C_1$–$C_8$-alkyl, aryl, vinyl or heteroaryl selected from the group consisting of pyridinyl, pyrimidinyl, pyrrolyl, thiophenyl, and furanyl, which may themselves be substituted by further substituents selected from the group consisting of linear and branched $C_1$–$C_8$-alkyl or $C_1$–$C_8$-aryl, linear and branched $C_1$–$C_8$-alkyloxy or $C_1$–$C_8$-aryloxy, halogenated linear and branched $C_1$–$C_8$-alkyl or halogenated $C_1$–$C_8$-aryl, linear and branched $C_1$–$C_8$-alkyl- or $C_1$–$C_8$-aryloxycarbonyl, linear and branched $C_1$–$C_8$-alkylamino, linear and branched $C_1$–$C_8$-dialkylamino, $C_1$–$C_8$-arylamino, $C_1$–$C_8$-diarylamino, formyl, hydroxyl, carboxyl, cyano, F, Cl, Br and I.

11. The process of claim 10, wherein the phosphine ligands used are triphenylphosphine, tri-(4-methoxyphenyl)phosphine, tricyclohexylphosphine or diphenylphosphinoferrocene.

12. The process of claim 10, wherein from 1 to 20 equivalents of phosphine based on the amount of transition metal are used.

13. The process of claim 1, wherein from 0.001 to 20 mol % of the transition metal catalyst based on the boronic acid derivative are used.

14. The process of claim 1, wherein the reaction proceeds in the presence of from one to twenty equivalents of water based on the boronic acid derivative.

15. The process of claim 1, wherein the reaction proceeds in an ether as a solvent.

16. The process of claim 1, wherein the reaction proceeds at a temperature between 0° C. and 80° C.

* * * * *

UNITED STATES PATENT AND TRADEMARK OFFICE
CERTIFICATE OF CORRECTION

| | | |
|---|---|---|
| PATENT NO. | : 6,864,394 B2 | Page 1 of 1 |
| APPLICATION NO. | : 10/477653 | |
| DATED | : March 8, 2005 | |
| INVENTOR(S) | : Goossen et al. | |

It is certified that error appears in the above-identified patent and that said Letters Patent is hereby corrected as shown below:

Column 8, Lines 63-64, "heated to to 60° C." should read -- heated to 60° C. --

Column 9, Lines 29-30, "heated to to 60° C." should read -- heated to 60° C. --

Column 15, Line 39, "substituent $R_1$" should read -- substituent $R^1$ --

Column 15, Line 62, "$R^3$ and $R^4$" should read -- $R^4$ and $R^5$ --

Signed and Sealed this

Twenty-second Day of May, 2007

JON W. DUDAS
*Director of the United States Patent and Trademark Office*